United States Patent [19]
Kuntz et al.

[11] 4,331,162
[45] May 25, 1982

[54] URINE SPECIMEN COLLECTING DEVICE AND METHOD OF USE

[75] Inventors: David H. Kuntz, Los Angeles; James A. Ingram, Costa Mesa, both of Calif.

[73] Assignee: SHS Enterprises, Ltd., Newport Beach, Calif.

[21] Appl. No.: 31,427

[22] Filed: Apr. 19, 1979

[51] Int. Cl.$^3$ .............................................. A61B 10/00
[52] U.S. Cl. .................................... 128/761; 128/295; 128/275
[58] Field of Search ........................ 128/295, 760–763, 128/275; 141/115, 331, 365; 4/301, 144.1, 144.2, 144.4; 73/421 R, 425.2 R, 425.4 R; 206/438, 569, 570; D7/63, 68

[56] References Cited
U.S. PATENT DOCUMENTS

| | | | |
|---|---|---|---|
| 3,252,683 | 5/1966 | Vetzmann | D7/43 |
| 3,561,427 | 2/1971 | Profy | 128/275 |
| 3,722,503 | 3/1973 | Hovick | 128/295 |
| 4,026,433 | 5/1977 | Crippe | 128/760 |
| 4,040,791 | 8/1977 | Kuntz | 128/761 |
| 4,064,760 | 12/1977 | Benjamin | 73/421 R |
| 4,176,412 | 12/1979 | Peterson | 4/144.1 |

*Primary Examiner*—Robert W. Michell
*Assistant Examiner*—J. L. Kruter
*Attorney, Agent, or Firm*—Henry M. Bissell

[57] ABSTRACT

A device for collecting a urine specimen, which is particularly adapted for females, is configured and adapted for use while the user is sitting on a toilet in the normal position for voiding. The device comprises a collector and a specimen container and selectively collects the clean, contaminant-free mid-stream portion of urine in the container. The urine specimen container is releasably secured to the collector at a bleed-off conduit extending from a collection exit in a uring receiving chamber of the collector. This exit is positioned in the chamber above a urine bleed-off exit in the conduit adapted for receiving and discarding the first-voided portion of urine at a controlled rate. The collection exit is remote from the bleed-off conduit exit, is shielded from urine splashing into the chamber, and is below a urine overflow exit in the chamber which leads to an overflow conduit. The chamber is preferably open topped and is adapted to be supported on the specimen container. A suitable handle extends radially outward from the chamber to facilitate holding the device in use. The handle and chamber configuration is symmetrical so as to be equally convenient for right-handed and left-handed users. The device is inexpensive, simple and disposable; and the chamber, bleed-off conduit, overflow conduit and handle can be integrally molded in a single operation. The specimen container and its lid can be separately formed. The entire structure is such that the lid can be easily sealed to the container after use and the collector thereafter removed and discarded.

32 Claims, 8 Drawing Figures

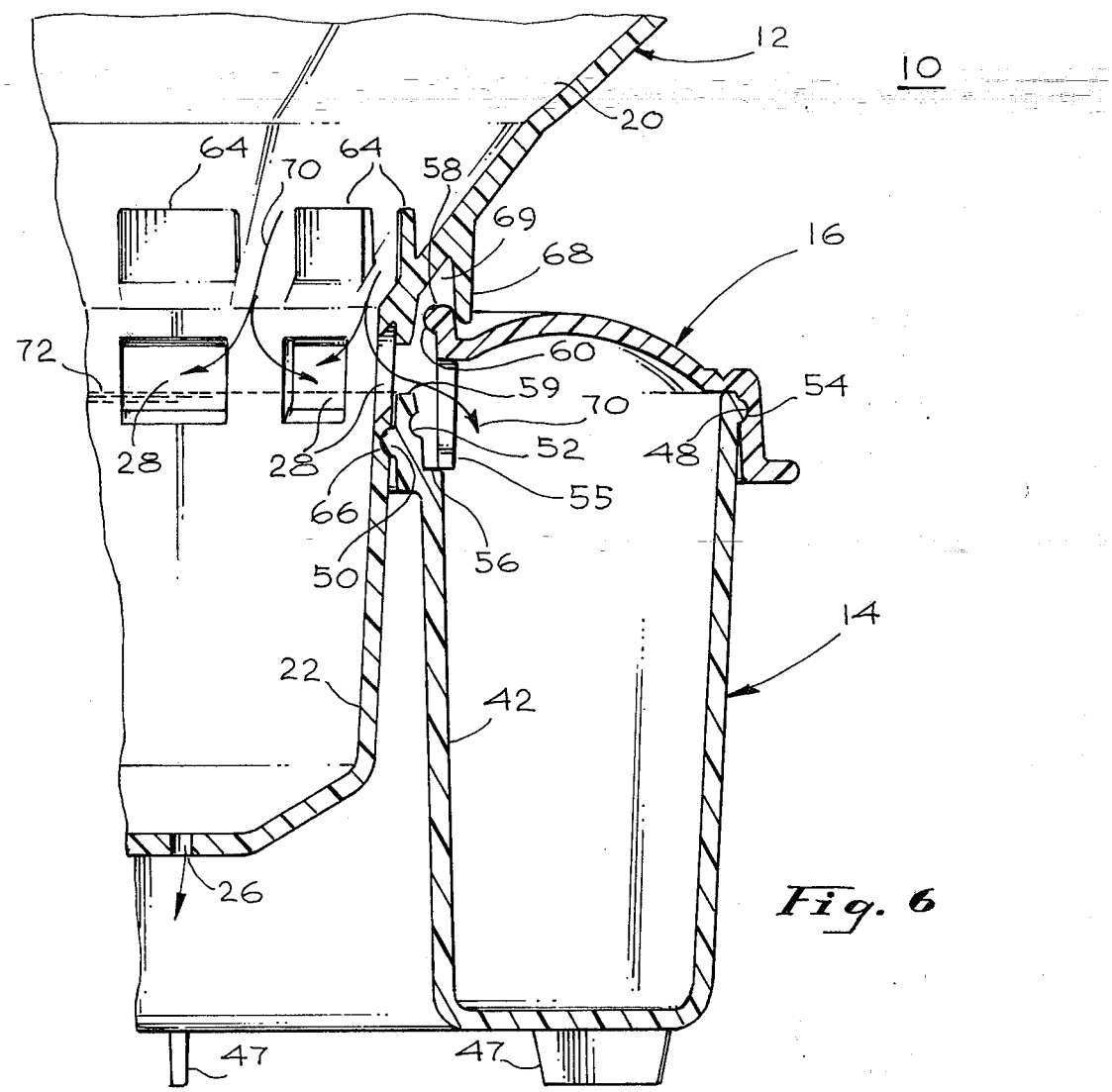
Fig. 6
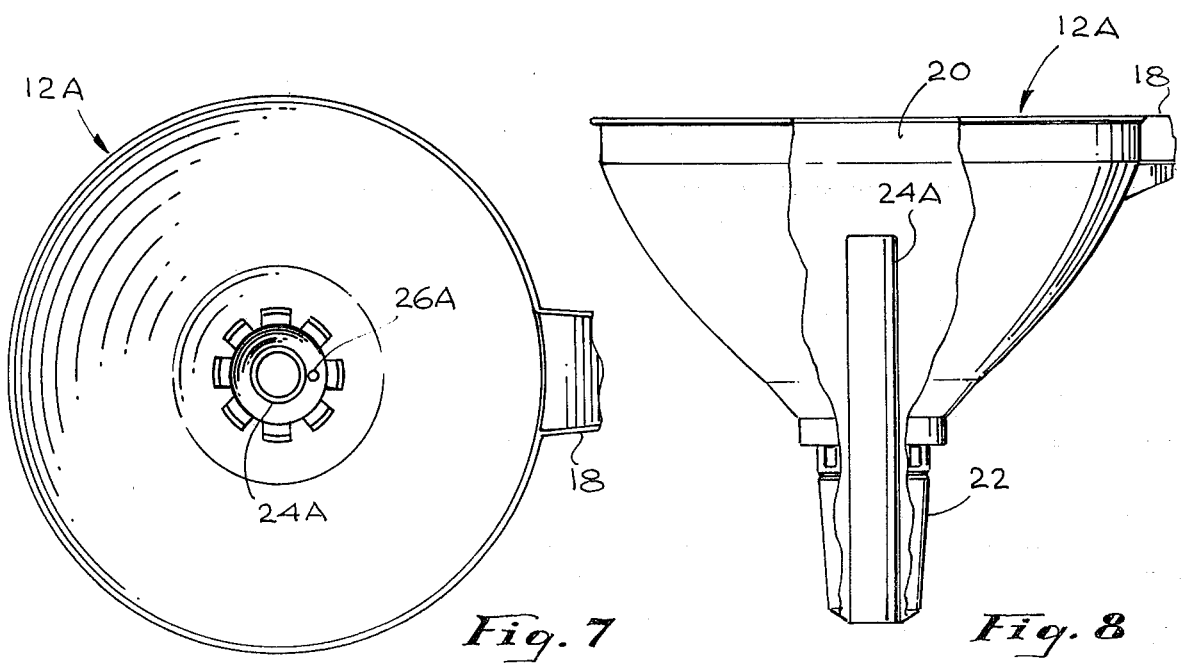
Fig. 7
Fig. 8

URINE SPECIMEN COLLECTING DEVICE AND METHOD OF USE

BACKGROUND OF THE INVENTION

1. Field of the Invention

This invention generally relates to specimen collecting devices and, more particularly, to portable urine specimen collection devices, particularly for use by females.

2. Description of the Prior Art

Urine analysis is such a simple, common and useful diagnostic aid that the taking of a urine specimen is generally included in even the simplest of physical examinations. It is important not only as an indicator or detector of certain physical conditions and diseases, but it is also particularly useful in connection with the treatment of infections related to the urinary tract, which are much more common in females than males. However, the problem of collecting a suitable specimen is considerably more complex when a female patient is involved.

Thus, in the collecting of a urine specimen from a female patient, it is important to take the specimen as a "mid-stream" sample. When a female patient voids in the normal manner, the initial portion is more likely to contain contain contamination from foreign matter than that portion which follows. This is because the initial portion is expelled with less force and usually is voided as a mere trickle which is likely to trail along the labia and pick up whatever contamination is present in those areas. The mid-stream portion is expelled with the greatest force and is most likely to leave the urethral meatus directly as a stream without contacting the labia or, if it does, the labia will have had most of the contamination washed off by the initial portion.

Some practitioners go to considerable lengths in an effort to obtain an uncontaminated urine sample from a female patient. With the patient in a reclining position, an attendant cleanses the area adjacent the urethral meatus with a suitable solution in an effort to wash off the contamination which is generally present in that area. Even with such precautions, however, contamination may develop in the collected urine sample to a level sufficient to give a false or misleading indication of the bacteria level in the sample. Moreover, taking a sample under such conditions is an extremely awkward and uncomfortable experience for the patient and is fairly costly, since the patient is required to be present in the physician's office or a hospital with a special attendant, usually a nurse, administering the procedure.

What has been needed is some simple but effective, fool-proof device, preferably disposable after a single use, which a patient can use with a minimum of instructions and without assistance, while voiding in the normal manner. The device should have the capability of receiving the entire amount of voided urine, rejecting the initial portion, selecting a portion corresponding to the mid-stream sample and transferring it to a specimen container, and rejecting the remainder of the voided urine by directing it, together with any overflow from the specimen container, into the toilet on which the patient is poitioned in the normal attitude.

Although the device set forth in U.S. Pat. No. 4,040,791 which issued on Aug. 9, 1977 to one of the applicants of the present application and is entitled Specimen Collecting Device accomplishes the foregoing objects, such device has been found to be somewhat complicated and expensive to manufacture. For example, it cannot be made in a single high-speed molding operation but bust be assembled from a plurality of parts. Moreover, it requires certain close tolerances which demand high quality control. Therefore it is not as simple and inexpensive as one would desire for a disposable device intended for extensive usage. Moreover, it is somewhat difficult to handle and orient while using it. Therefore, it would be desirable to provide an improved device of the same general type which would be as efficient but less expensive, and easier to handle, orient and use.

SUMMARY OF THE INVENTION

The foregoing objects have been achieved by the improved device of the present invention. The device is substantially as set forth in the Abstract above. Not only is it very simple, but it can be rapidly manufactured into a unitary product in a single low-cost molding operation, preferably from inexpensive material, such as plastic, rubber or the like. Moreover, it is highly efficient in isolating and collecting contaminant-free urine. The device is particularly adapted for convenient use by a female patient while she is sitting on a toilet. Thus, she can void urine into the device, and the desired mid-stream sample of urine can be easily and automatically collected. For such purposes the improved device of the invention comprises a collector and a specimen container, the collector comprising a urine-receiving chamber having a urine-receiving opening at its upper end and three urine exits at different levels. The first exit is adjacent the lower end of the chamber in a downwardly depending exit conduit. This is for bleeding first-voided urine from the collector at a slow controlled rate into the toilet so that as voiding continues the urine level rises to the second exit which is above the first exit and preferably shielded from the first-voided urine. Thus, the second exit passes clean, contaminant-free mid-stream urine to a detachable urine specimen container positioned to receive urine from the second exit. As voiding continues the urine level in the chamber may rise above the second exit, particularly when the specimen container becomes filled. If the urine level reaches the height of the third exit (above the level of the second exit) excess urine passes through that exit and, via an overflow conduit, to the toilet. Thus, only the clean mid-stream urine is retained in the specimen container. At cessation or diminishing of voiding rate, the excess urine trapped in the chamber below the third exit level bleeds out through the first exit until only the urine sample in the specimen container remains.

In one preferred arrangement in accordance with the invention, the collector (apart from the specimen container) is much like a funnel in configuration with a handle extending from the edge thereof. The cone-shaped portion of the funnel corresponds to the collection chamber; the lower central tube of the funnel constitutes the bleed-off conduit and is closed off at the lower end thereof except for an aperture of limited size to control the bleed-off of the first-voided urine at a limited rate. Near the juncture of the collection chamber and the bleed-off conduit is a plurality of apertures or windows, equally spaced about the periphery of the bleed-off conduit, constituting the second exit for communicating with and transferring urine to a specimen container when the specimen container is in place. The specimen container is toroidal in planar cross-section, has both inner and outer walls, and (when mounted together with the collector) surrounds the bleed-off conduit. The specimen container is provided with a flexible lid having a central opening. Mating lip and recess surfaces around the periphery of the specimen container and lid, respectively, provide an effective circumferential seal between lid and container. The portion of the lid surrounding the central opening is spaced upwardly from the upper end of the inner wall of the container, thus defining a circumferential opening which is adjacent the windows at the base of the cone-shaped portion of the collector so as to admit urine therethrough. A mating ring and recess serve to retain the specimen container on the bleed-off conduit, while permitting the collector and container to be separated easily, when desired. Preferably a plurality of upwardly extending shields or dams are located about the base of the collecting chamber in registration with the second exit apertures so as to shield those apertures from urine being voided into the collector until after the first-voided portion fills the bleed-off conduit.

An overflow conduit connecting with the chamber at an overflow exit positioned significantly above the second exit is provided to remove any excess urine from the collector and prevent it from running over its uppermost rim. This overflow exit is also provided with a shield to block urine as voided from passing through the overflow exit.

In a first alternative arrangement of the preferred embodiment, the overflow exit and overflow conduit connect to the side of the collection chamber in a position radially displaced from the central axis of the device.

In a second alternative arrangement, the overflow conduit is centrally positioned as a standpipe extending upwardly from the closed off exit of the bleed-off conduit. In the latter case, the bleed-off exit opening may be radially displaced and positioned between the wall of the overflow conduit and the inner wall of the bleed-off conduit.

In accordance with an aspect of the invention, the flexible lid of the specimen container and the upper edge of the inner wall of the container are configured to mate in sealing relationship when the central portion of the lid is pushed downwardly to engage the inner wall of the container. This serves to complete the closure of the specimen container after the selected urine sample has been collected therein.

To facilitate the sealing operation, the height of the specimen container is made to exceed the length of the bleed-off conduit by approximately ¼ to ½ inch. The collector is provided with a circumferential shoulder surrounding the bleed-off conduit near the juncture of the bleed-off conduit and the collection chamber. This shoulder is provided with a circumferential recess capable of receiving the upper edge of the inner wall of the specimen container when the two are pushed together. When this is done, the central ring portion of the flexible lid is pushed downwardly to engage a circumferential lip surrounding the inner wall of the container, this retaining the central portion of the lid in the downward position and effectively closing off and sealing the circumferential opening which previously existed between the lid and the upper edge of the inner wall of the container.

By virtue of this arrangement, it is intended that after the patient has used the collector device and left it for the nurse or other medical assistant, the nurse simply pushes downward on the upper circumferential edge of the cone-shaped collecting chamber, thereby driving the lid of the specimen container into sealing relationship with the inner wall of the container. This not only serves to seal the previously existing opening between the lid and the inner wall, but it reinforces the outer circumferential seal between the lid and the outer wall of the container by developing a downward bias on the lid. Thereafter, the nurse simply grasps the specimen container and lid with one hand and removes the collector portion by pulling it upward and away from the specimen container portion. Later, when it is desired to open the specimen container, the lid is simply unsealed by lifting upward relative to the specimen container at the circumferential edge thereof. This serves to release both the inner and outer seals so that the lid can be removed from the container. These various features and aspects of the present invention result in an improved urine specimen collecting device which is extremely effective in collecting the desired contaminant-free midstream portion during use, is readily sealable and separable for retention of the specimen container while the collector proper can be thrown away, is simple, lightweight, cheap to manufacture and easy to use without elaborate instruction.

BRIEF DESCRIPTION OF THE DRAWING

A better understanding of the present invention may be had from a consideration of the following detailed description, taken in conjunction with the accompanying drawing, in which:

FIG. 6 is a sectional view similar to FIG. 5, showing the assembly of the various elements making up the arrangement of the invention;

FIG. 7 is a plan view of an alternative embodiment of the invention; and

FIG. 8 is an elevational view, partially broken away, of a portion of the alternative embodiment of FIG. 7.

DESCRIPTION OF THE PREFERRED EMBODIMENTS

Figure 1:
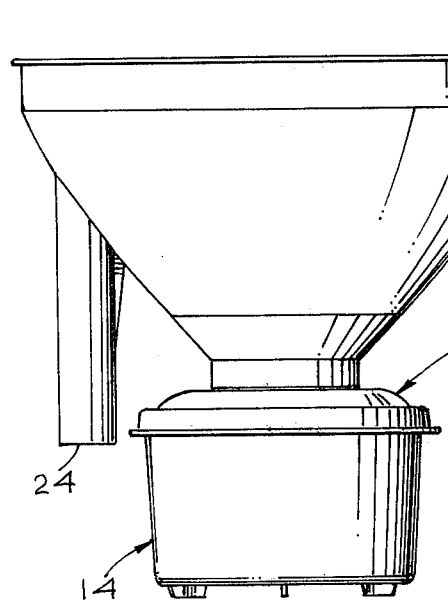
FIG. 1 is an elevational view of one particular arrangement in accordance with the invention.
Figure 2:
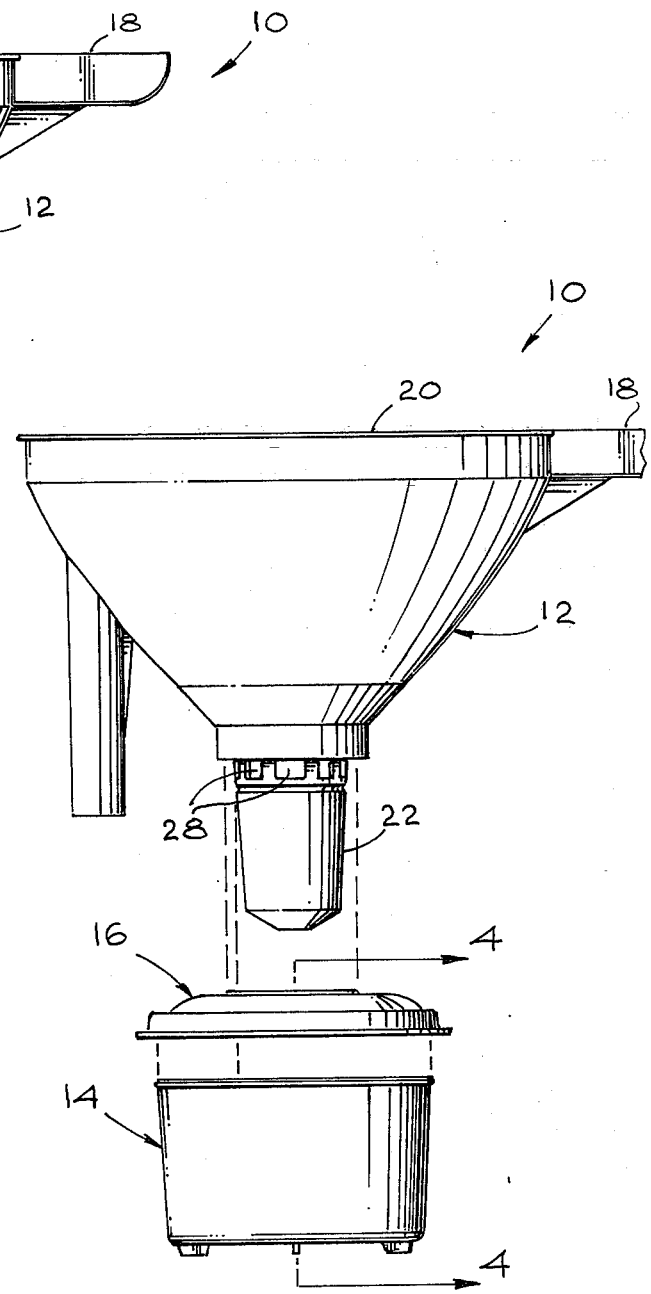
FIG. 2 is an exploded view of the arrangement shown in FIG. 1.
Figure 3:
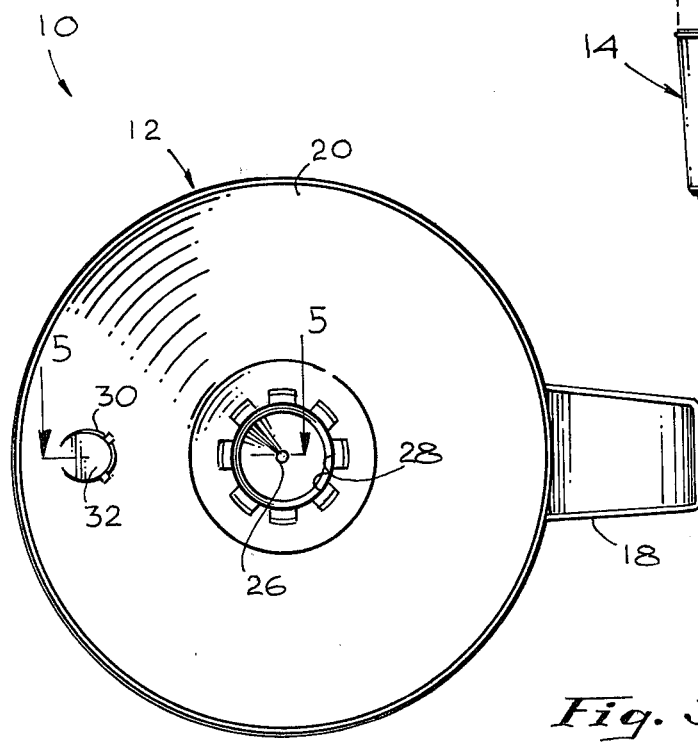
FIG. 3 is a plan view of the arrangement of FIG. 1.

One preferred embodiment of the present invention is depicted in FIGS. 1-3 of the drawings. As is shown particularly in the exploded view of FIG. 2, the collecting device 10 comprises a collector 12, specimen container 14 and specimen container lid 16.

The collector 12 is a generally funnel-shaped element having a handle 18, a cone-shaped receiving chamber 10, a bleed-off conduit 22 at the lower end of the cone-shaped receiving chamber 20, and an overflow conduit 24 which extends through the sidewall of the receiving chamber 20 and is attached thereto.

The collector 12 is provided with three exits for the release of urine therefrom. The first exit is a bleed-off exit 26 comprising a small hole at the bottom of the bleed-off conduit 22, the bottom of which is otherwise closed off and thereby constitutes a pocket or recess for receiving the first-voided urine from the chamber 20. The second exit comprises a plurality of apertures or windows 28 near the bottom of the cone-shaped portion of the chamber 20. As will be shown in detail hereinbelow, these windows 28 communicate with the interior of the specimen container 14 when the constituent elements are assembled in the configuration shown in FIG. 1. A third exit 30 is located in the side of the chamber 20 above the second exit 28 and communicates with the interior of the overflow conduit 24. The overflow exit 30 is provided with a shield a shield 32 to block the overflow of urine via that exit 30 until the urine level in the collector 12 rises to the overflow exit 30.

Figure 4:
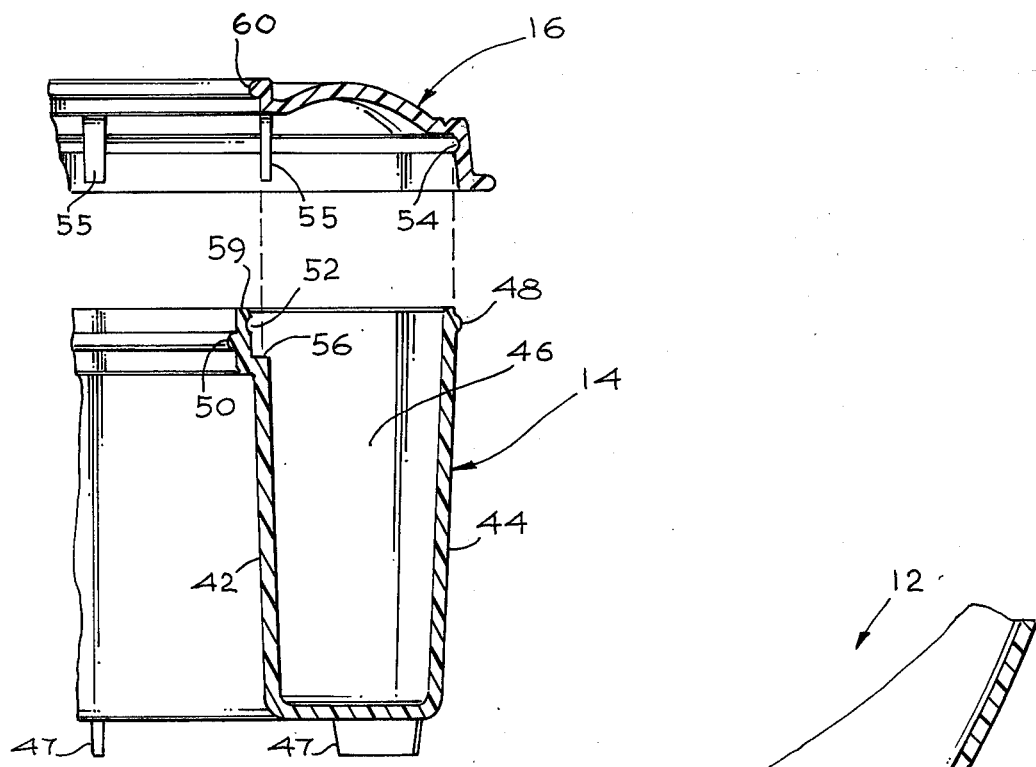
FIG. 4 is a quarter-sectional view of a portion of the arrangement depicted in FIG. 2, taken along the line 4—4 thereof.

As seen in FIG. 4, which is a quarter-sectional view of a portion of the arrangement of FIG. 2, taken along the line 4—4 and looking in the direction of the arrows, the specimen container 14 is somewhat toroidal in form, having an upstanding hollow center section surrounded by an inner cylindrical wall 42 and an outer cylindrical wall 44. The storage space for urine collected in the container 14 is between the inner and outer walls 42, 44. This space 46 is open at the top of the container 14. Legs 47 are mounted at the base of the container 14.

Near the top of the outer cylindrical wall 44 is an outwardly protruding lip or rim 48 which extends circumferentially about the specimen container 14. A similar protruding lip or rim 50 projects radially inwardly from the inner wall 42 and extends circumferentially about the hollow space defined by the wall 42. Near the top of the wall 42 in the side facing the space 46 is a recess or slot 52 which extends circumferentially about the specimen container inner wall 42.

The lid 16 is provided with an inner circumferential recess 54 which serves to mate with the rim 48 of the container 14 when the lid 16 is mounted on the container 14, thus retaining the lid thereon in sealing relationship about the outer edge of the container 14. The lid 16 is provided with a plurality of downwardly depending, projecting stop pins 55 which, when the lid 16 is first placed on the container 14, bear against a ledge 56 on the inner wall 42 of the container 14 and maintain a space between the ring 58 about the central opening of the lid 16 and the upper edge 59 of the inner wall 42 of the container 14. These stop pins 55 are flexible, as is the lid 16, so that upon the application of downward force sufficient to bend the pins 55, they give way and permit an inwardly projecting rim 60 of the lid 16 to move downwardly into engagement with the circumferential recess 52, thus establishing a seal between the inner rim 60 of the lid 16 and the upper end of the inner wall 42 of the container 14. When mounted in such fashion, the storage space 46 for the urine which is collected in the container 14 is completely sealed—at the outer edge by the seal between the outer rim 48 and the recess 54, and at the inner edge by the seal between the inner rim 60 and the recess 52.

Figure 5:
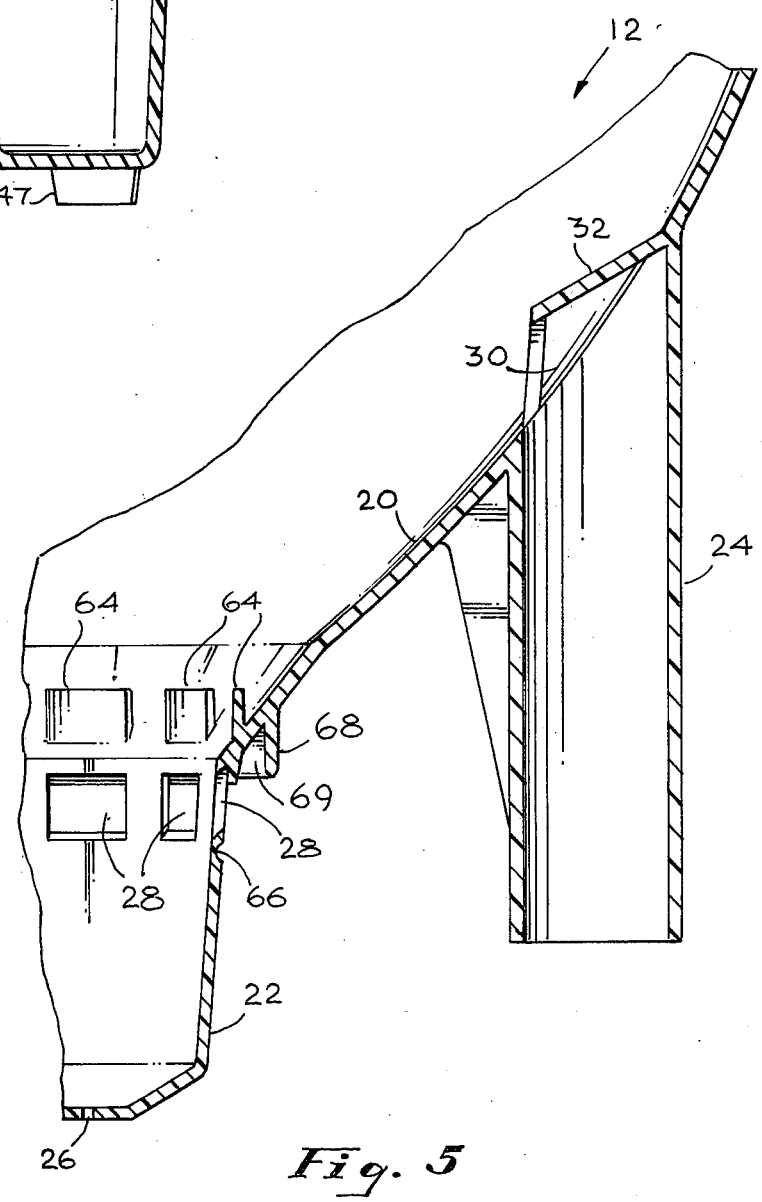
FIG. 5 is a quarter-sectional view of a portion of the arrangement of FIG. 1, taken along the line 5—5 of FIG. 3.

Referring now to FIG. 5, a sectional view taken along the line 5—5 of FIG. 3 and looking in the direction of the arrows, certain structural details of the collecting device of our invention are shown therein. FIG. 5 shows the sidewall of the receiving chamber 20 in the region of the overflow conduit 24 and the collecting exit comprising the windows or apertures 28. The overflow exit 30 may be seen extending through the sidewall of the receiving chamber 20 and communicating with the overflow conduit 24. As shown, the exit 30 is protected by the shield 32 to minimize the splashing of urine through the exit 30. Shields or barriers 64 serving as tiny dams are mounted respectively above the windows 28 to interfere with the flow of the first-voided urine through the windows 28. These barriers 64 channel the urine through the passages between adjacent barriers 64, thus diverting the urine from the windows 28 until the urine rises in the bleed-off conduit 22 to the level of the windows 28.

The sidewall of the bleed-off conduit 22 is provided with a circumferential recess 66 positioned just below the windows 28. This serves to receive the inner rim 50 of the container 14, thus retaining the container 14 in sealing relationship to the collector 12 when the two are affixed together. Of course, the lid 16 will be positioned between the collector 12 and container 14 when mounted in this fashion (see FIG. 6).

The collector 12 is provided with a downwardly depending, circumferential skirt or lip 68 which defines, with the wall of the bleed-off conduit 22, a circumferential recess 69.

FIG. 6 is a sectional view similar to that of FIG. 5 but showing the container 14, lid 16 and collector 12 assembled together as prepared for shipment and for operative use in selectively collecting a mid-steam urine specimen. The lid 16 is shown in place on the container 14 with the outer periphery of the lid sealed to the container 14 by virtue of the mating of the rim 48 in the circumferential recess 54. Similarly, the inner wall of the specimen container 14 is sealably engaged to the bleed-off conduit 22, and thereby retained thereon, by the mating relationship of the inner rim 50 in the circumferential recess 66. The central circmferential ring 58 of the cover 16 surrounding the central opening thereof is partially within the recess 69 and bearing against the skirt 68. A stop pin 55 is shown bearing against the ledge 56, thus maintaining the space between the upper edge 59 of the wall 42 and the lid 16. This space is adjacent the windows 28 and extends circumferentially about the assembly, interrupted only by the spaced-apart pins 55.

When the collector device is used by a patient, urine is voided into the receiving chamber 20 of the collector 12. The first-voided urine flows down into the bleed-off conduit 22 and begins bleeding out the bleed-off exit opening 26; if the urine initially drops onto the wall of the receiving chamber 20, it flows down the wall and in the channels between the barriers or dams 64, as indicated by the arrows 70. When the urine level rises to the windows 28, as indicated by the line 72, urine then begins flowing through the windows 28 and through the entrance space between the lid 16 and the inner wall 42 of the specimen container 14, as further indicated by the arrows 70. As voiding continues, the mid-stream portion of the voiding is directed in the manner described into the specimen container 14. As the specimen container 14 fills with urine, the air which was initially in the empty container 14 is permitted to escape out the same entrance space and the windows 28. Further voiding after the specimen container 14 is full backs up into the receiving chamber 20 until the level of the overflow exit 30 (FIG. 5) is reached, after which the overflow urine runs out the overflow conduit 24. When voiding is terminated, the urine remaining in the collector bleeds off through the bleed-off conduit 22 and exit 26, until the collector 12 is emptied.

At this point, the patient will normally deliver the collector and specimen container with the specimen contained therein to the nurse or other medical assistant who thereafter places the device 10 on a counter, table or other horizontal surface and bears down on the upper edge of the collector 12. This causes skirt 68 to bear down against the adjacent surface of the lid 16 as the ring 59 of the lid moves further into the recess 69 and causes the semi-flexible pins 55 to bend and slip off the ledge 56. Further downward movement of the collector 12 relative to the specimen container 14 causes the inner rim 60 of the lid 16 to move downwardly into engagement with the circumferential recess 52, effecting the seal between the rim 60 and the recess 52 and thus preventing any escape of the specimen collected within the container 14. The collector 12 is then pulled upwardly, relative to the lid 16 and container 14, releasing the retention of the container 14 on the bleed-off conduit 22 at the recess 66 and separating the collector from the specimen container. The collector 12 is then discarded and the specimen container retained for processing of the collected specimen.

An alternative embodiment of the invention is shown in FIGS. 7 and 8. In this embodiment, the elements of the collecting device 1 are the same as shown in FIGS. 1-6, except that the oveflow conduit 24A is centrally located within the bleed-off conduit 22. The bleed-off exit opening 26A is shown at the bottom of the bleed-off conduit 22 (see FIG. 7) but located between the wall of the overflow conduit 24A and the inner wall of the bleed-off conduit 22. The bottom of the overflow conduit 24A is of course open to permit the escape of urine overflowing through the conduit 24A. Utilization of this alternative embodiment of the collector 12A, when assembled in combination with the specimen container 14 and the lid 16, is the same as has been described for the use of the embodiments of FIGS. 1-6.

Arrangements in accordance with the present invention are particularly effective in the collection of the preferred mid-stream portion of voided urine for transfer to and retention in a specimen container. The collecting device is simple to use without the need for any special instructions and its utilization is virtually foolproof. After the device is used by the patient, sealing of the specimen container and lid with removal of the collector from the specimen container is virtually automatic by any personnel without the need for any special training. The various components of the device are preferably molded from high density polyethylene with a wall thickness of 0.035 inches, although other materials may be used, as appropriate. The molding operation is simple and the cost of the manufactured product is low so that the device is readily disposable after a single use. During manufacture the components of the device are readily sterilized so that the device can simply be unwrapped, used and thrown away without the necessity of on-site sterilization procedures.

Although there have been described above specific arrangements of an improved urine specimen collecting device in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. A urine specimen collecting device for selectively collecting a mid-stream portion of voided urine, the device comprising in combination:

a collector having first, second and third exits for different portions of the voided urine, the first exit being positioned near the bottom of the collector for bleeding off the first-voided urine, the second exit being positioned above the first exit for transferring the desired mid-stream portion of urine to an associated specimen container, the third exit being positioned above the second exit for transferring excess urine from the collector;

a bleed-off conduit extending between the first and second exits of the collector;

a generally toroidally-shaped specimen container configured for releasable mounting on the bleed-off conduit in position surrounding said conduit for receiving urine flowing through the second exit; and a flexible lid sealingly mounted on the specimen container about the periphery thereof and having a central ring opening spaced from the container to define an opening adjacent the second exit for receiving a specimen of urine into the container.

2. The device of claim 1 wherein the collection chamber is generally funnel-shaped with a cone-shaped side wall portion constituting a receiving chamber and a downwardly depending tubular portion connected to the receiving chamber and constituting the bleed-off conduit, the bleed-off conduit being closed off at its lower end except for a bleed-off exit of limited opening size to limit the range of urine flow therethrough.

3. The device of claim 2 wherein the second exit comprises a plurality of circumferentially spaced windows extending about the collector at the juncture between the bleed-off conduit and the receiving chamber.

4. The device of claim 3 further including means for diverting urine from the receiving chamber away from said windows until the bleed-off conduit is filled with the first-voided portion.

5. The device of claim 4 wherein said means comprise upstanding barrier means extending upwardly from the collector wall above the windows and individually associated therewith, said barriers defining channels for the urine to flow therebetween.

6. The device of claim 2 wherein the third exit includes an overflow conduit extending downwardly from a sidewall of the receiving chamber and having an overflow exit extending through the sidewall and communicating between the receiving chamber and the overflow conduit.

7. The device of claim 6 further comprising a shield extending over and partially closing off the overflow exit to prevent the splashing of liquid therethrough.

8. The device of claim 2 wherein the third exit comprises an overflow conduit which is centrally located along the axis of the collector and extends upwardly from the closed-off bottom of the bleed-off conduit into the receiving chamber.

9. The device of claim 8 wherein the bleed-off exit at the bottom of the bleed-off conduit is positioned between the overflow conduit and the inner wall of the bleed-off conduit.

10. The device of claim 1 wherein the specimen container includes inner and outer circumferential walls defining a specimen storage space closed at the bottom and open at the top, the inner wall defining a hollow open space and having an inwardly directed, circumferential rim near the upper end of the inner wall for engaging a mating circumferential recess on the bleed-off conduit of the collector.

11. The device of claim 10 wherein the outer wall includes an outwardly extending circumferential rim near the upper end of the outer wall for engaging a mating circumferential recess in the inner surface of the lid about the periphery thereof.

12. The device of claim 11 wherein the inner wall is provided with a circumferential recess near the upper end of the wall for sealingly engaging a mating portion of the container lid.

13. The device of claim 12 wherein the inner wall is provided with a circumferential ledge below said circumferential recess for supporting spacing means extending from the lid in order to define the opening for receiving urine transferring to the container from the collector second exit.

14. The device of claim 12 wherein the lid is flexible and comprises a downwardly depending outer wall having a circumferential recess extending about the inner surface thereof for mating in sealing relationship with the corresponding circumferential rim of the container.

15. The device of claim 14 wherein the lid further comprises an inner circumferential ring defining a central opening, said ring having an inwardly projecting circumferential rim for mating in sealing relationship with a corresponding circumferential recess extending about the inner wall of the container.

16. The device of claim 15 wherein the lid further comprises spacing means projecting downwardly to engage a ledge of the container for defining a circumferential opening for admitting urine into the container.

17. The device of claim 16 wherein said spacing means comprise a plurality of spaced-apart semi-flexible pins for permitting the ring portion of the lid to be moved downwardly relative to the container under the application of force sufficient to overcome the resistance of the semi-flexible pins, whereby the ring portion of the lid is permitted to close the central circumferential opening between the lid and container and to seal the lid to the inner wall of the container.

18. The device of claim 14 wherein the collector further comprises a circumferentially extending, downwardly directed skirt configured to bear against the central portion of the lid upon the application of force upon the collector in the direction toward the container to deflect the inner portion of the lid into sealing engagement with the inner wall of the container.

19. The device of claim 1 further comprising an outwardly directed, radially extending handle attached to the outer periphery of the collector adjacent the upper rim thereof, said handle and collector being symmetrically configured to facilitate use by either right-handed or left-handed users with equal convenience.

20. The device of claim 10 further comprising support members appended to the bottom of the specimen container and wherein the bleed-off conduit of the collector terminates a predetermined distance above the support members sufficient to permit downward motion of the collector to the position at which the central ring opening of the lid engages the inner wall of the container.

21. The device of claim 1 wherein the specimen container includes inner and outer circumferential walls defining a specimen storage space closed at the bottom and open at the top, the inner wall defining a hollow open space for receiving a portion of the bleed-off conduit therein, and mating surface engaging means for selectively sealing the outer peripheral edge of the lid to the outer wall of the container and the central ring opening of the lid to the inner wall of the container.

22. A container for receiving and storing pourable material therein comprising inner and outer circumferential walls defining a storage space between them which is closed at the bottom and open at the top, the inner wall defining a hollow open space;
   a flexible lid for releasably mounting on said container in sealing relationship therewith, the outer peripheral portions of the lid and container having mating surfaces for releasably interlocking adjacent portions in sealing relationship, said lid including an inner circumferential ring defining a central opening, the lid and inner wall of the container having mating surfaces for interlocking together in sealing relationship; and
   means for spacing the central portion of the lid apart from the inner wall of the container in a first position of the lid, said means defining an opening between the lid and the inner wall of the container for transferring material through said opening between the interior and exterior of the container.

23. The device of claim 22 further comprising a specimen collector mounted coaxially with the container and having a receiving chamber with a transfer exit adjacent the opening between the lid and the container for collecting a selected liquid specimen and transferring it to the container through said opening.

24. The device of claim 23 wherein the collector is generally funnel-shaped and includes a first exit below said opening for bleeding from the collector a first portion of liquid received in the receiving chamber and an overflow exit opening through a wall of the receiving chamber above the transfer exit for removing any excess liquid from the collector.

25. The device of claim 24 wherein the collector further comprises an outer projecting wall mounted adjacent the inner circumferential ring of the lid and shaped to bias the ring into sealing engagement with the inner wall of the container.

26. The method of using a urine specimen collector to collect and seal a selected portion of voided urine in a specimen container while protecting the specimen from extraneous contamination, comprising the steps of:
   receiving urine during voiding in a generally funnel-shaped collector with tapered walls and a central tubular conduit depending downwardly from said walls;
   bleeding the initial portion of the voided urine out of the collector through a restricted opening in a lower porion of said conduit;
   transferring a selected portion following the initial portion of urine from an upper portion of the conduit to an annular container releasably retained in position surrounding the tubular conduit, the container having a lid with a downwardly depending outer edge and a circumferential recess along the inner surface of the outer edge for for sealingly receiving a mating protruding peripheral rim of the container, the lid further defining a central opening surrounded by a radially inwardly protruding lip for sealingly mating with a radially outwardly directed circumferential recess in the container wall, the lid being formed of a resiliently flexible material and, in its relaxed position with its outer edge mated to the container peripheral rim, the portion adjacent the central opening being spaced from the container to define an opening between the lid and the container wall for receiving the selected portion of urine transferred from the conduit;

discarding all urine voided into the collector except the selected portion retained in the container; and sealing the selected portion within the container by pushing the collector and container together until the protruding lip surrounding the central opening of the lid snaps into mating and sealed position with the recess in the container wall.

27. The method of claim 26 further including separating the collector and the container and discarding the collector.

28. The method of claim 26 wherein the sealing step comprises placing the container with the collector on a horizontal surface and pressing down on the collector, thereby forcing the lid portion adjacent the central opening toward the container inner wall and into a position encircling the upper edge of said inner wall.

29. The method of claim 28 wherein the separating step comprises grasping the collector and container in both hands and pulling them apart while leaving the container lid sealingly engaged with the container at both the inner lip-and-recess mating surfaces and the outer recess-and-rim mating surfces.

30. The method of claim 26 comprising using the collector while seated in conventional fashion on a toilet with urine discarded from the collector being directed into the toilet bowl.

31. The method of claim 26 wherein the urine discarding step includes permitting any urine remaining in the collector after the specimen is collected to drain out through the restricted opening in the conduit.

32. The method of claim 26 further including permitting voided urine in excess of a predetermined amount related to the rate of voiding, the bleed rate and the transfer rate to exit the collector along an overflow path provided by the collector.

* * * * *